United States Patent [19]

Krämer et al.

[11] 4,232,033
[45] Nov. 4, 1980

[54] COMBATING FUNGI WITH DIASTEREOMERIC FORM A OF 1-PHENOXY-3,3-DIMETHYL-1-(1,2,4-TRIAZOL-1-YL)-BUTAN-2-OLS

[75] Inventors: Wolfgang Krämer; Karl H. Büchel; Wolf-Dietrich Pflugbeil, all of Wuppertal; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 941,832

[22] Filed: Sep. 11, 1978

[30] Foreign Application Priority Data

Sep. 29, 1977 [DE] Fed. Rep. of Germany ....... 2743767

[51] Int. Cl.$^3$ .................... A01N 43/64; C07D 249/08
[52] U.S. Cl. ..................................... 424/269; 548/262
[58] Field of Search .................. 260/308 R; 424/269; 548/262

[56] References Cited

U.S. PATENT DOCUMENTS 3,952,002   4/1976   Kramer et al. ................. 260/308 A

OTHER PUBLICATIONS

Karrer, Organic Chemistry, (2nd Ed., New York, 1946), pp. 92–102.
Burger, Medicinal Chemistry, (2nd Ed., New York, 1960), pp. 44–45.

*Primary Examiner*—Alton D. Rollins
*Attorney, Agent, or Firm*—Sprung, Felfe, Horn, Lynch & Kramer

[57] ABSTRACT

Substantially pure diastereomeric form A of 1-phenoxy-3,3-dimethyl-1-(1,2,4-triazol-1-yl)-butan-2-ols of the formula

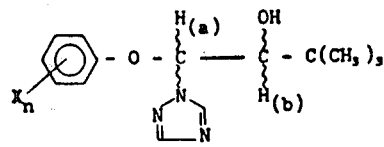

in which X represents halogen, optionally substituted p- or m-phenyl, substituted o-phenyl, alkyl, alkoxycarbonyl or nitro, and n represents an integer from 1 to 5, which possess fungicidal properties.

7 Claims, No Drawings

COMBATING FUNGI WITH DIASTEREOMERIC FORM A OF 1-PHENOXY-3,3-DIMETHYL-1-(1,2,4-TRIAZOL-1-YL)-BUTAN-2-OLS

The present invention relates to and has for its objects the provision of substantially pure diastereomeric form A of various 1-phenoxy-3,3-dimethyl-1-(1,2,4-triazol-1-yl)-butan-2-ols which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that diastereomer mixtures of triazolyl-O,N-acetals as well as individual diastereomeric triazolyl-O,N-acetals in general exhibit a fungicidal activity (see U.S. Pat. No. 3,952,002, issued Apr. 20, 1976).

The present invention now provides, as new compounds, the enantiomer pairs of the diastereomeric forms A (see explanation below) of the triazolyl-O,N-acetals of the general formula

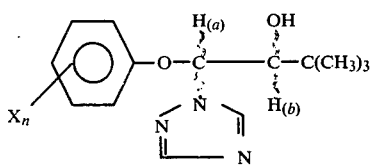

in which

X represents halogen, optionally substituted p- or m-phenyl, substituted o-phenyl, alkyl, alkoxy-carbonyl or nitro and n represents an integer from 1 to 5.

Preferably, X represents fluorine, chlorine, bromine, iodine, p- or m-phenyl (optionally substituted by fluorine, chlorine or bromine), o-phenyl (substituted by fluorine, chlorine or bromine), straight-chain or branched alkyl with 1 to 4 carbon atoms, alkoxycarbonyl with 1 or 2 carbon atoms in the alkyl part or nitro, and n represents 1, 2 or 3.

The following compounds, which are distinguished by a particularly good activity, should be mentioned: 1-(4-chlorophenoxy)-3,3-dimethyl-1-(1,2,4-triazol-1-yl)-butan-2-ol and 1-(4-biphenylyloxy)-3,3-dimethyl-1-(1,2,4-triazol-1-yl)-butan-2-ol.

By way of explanation, the following should be noted. Compounds with two asymmetric carbon atoms can exist in the two diastereomeric forms, namely the threo form and the erythro form. In the case of the compounds according to the invention, attribution is only possible with provisos, because the absolute configuration has not yet been determined; this fact is expressed by the wavy lines in formula (I). Accordingly, a differentiation is made here between form A and form B, which can be unambiguously characterized in accordance with their physico-chemical properties, the more hydrophilic form, characterized by lower coupling constants of the protons $H_{(a)}$ and $H_{(b)}$ in the NMR spectrum, being designated form A.

Surprisingly, the diasteromeric forms A of the triazolyl-O,N-acetals of the formula (I) exhibit a substantially greater activity against fungal plant diseases than the diastereomer mixtures, known from the prior art, of triazolyl-O,N-acetals. The compounds according to the invention thus represent a valuable enrichment of the art.

It was in no way to be expected from the prior art that the forms A of the triazolyl-O,N-acetals of the formula (I) would be distinguished by very good fungicidal properties while the analogous forms B of these compounds are only slightly active as fungicides.

The invention also provides a process for the preparation of the diastereomeric form A of a triazolyl-O,N-acetal of the formula (I), in which a triazolyl-ketone of the general formula

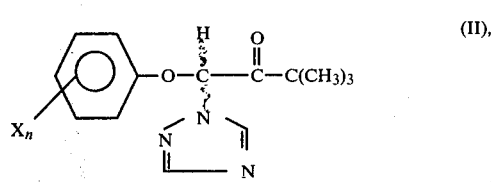

in which X and n have the above-mentioned meanings, is stereoselectively reduced with a secondary alcoholate in the presence of a diluent.

If 1-(4-chlorophenoxy)-3,3-dimethyl-1-(1,2,4-triazol-1-yl)-butan-2-one and aluminium isopropylate are used as starting materials, the course of the reaction can be represented by the following equation:

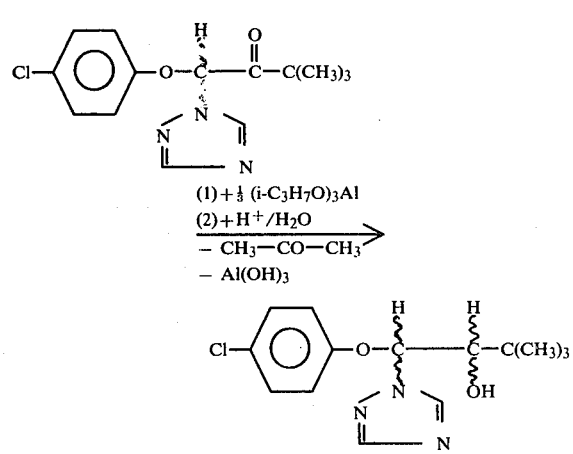

The starting materials of the formula (II) are known (see U.S. Pat. No. 3,952,002, issued Apr. 20, 1976 and U.S. application Ser. No. 779,861, filed Mar. 21, 1977). They are obtained in accordance with the processes described there, by reacting the appropriately substituted 1-aryloxy-1-halogeno-3,3-dimethyl-butan-2-ones with 1,2,4-triazole, optionally in the presence of an acid-binding agent, at temperatures between 60° and 120° C.

The compounds which follow in Table 1 may be mentioned specifically as examples of the triazolyl-ketones of the formula (II) to be used as starting materials, according to the invention:

TABLE 1

Structure (II): Phenyl ring with $X_n$ substituents, connected via -O-C(H)- to -C(=O)-C(CH₃)₃, with triazole (N=N-N) group on the central carbon.

| $X_n$ | Melting point (°C.) or boiling point (°C./mm Hg) |
|---|---|
| 4-Cl | 75 |
| 4-C₆H₅ (4-phenyl) | 105–106 |
| 4-Br | 89–92 |
| 4-F | 160/0.3 |
| 4-NO₂ | 145 |
| 4-C(CH₃)₃ | 115 |
| 2,6-Cl₂ | 186 |
| 2,5-Cl₂ | 110 |
| 3-CH₃,4-Cl | 88–89 |
| 2-CH₃,5-Cl | 114 |
| 2-CH₃,4-Cl | 94–96 |
| 2,3-(CH₃)₂ | 76 |
| 4-I | 107–108 |
| 2-CH₃ | 142–150 |
| 3-CH₃ | 70–72 |
| 2-F | 73–74 |
| 3-Br | 79–80 |
| 2-NO₂ | 90–93 |
| 3,4-(CH₃)₂ | 71–73 |
| 4-Cl, 3,5-(CH₃)₂ | 101 |
| 2,4,5-Cl₃ | 142–145 |
| 2-Cl | 110 |
| 4-C₃H₇-i | 76 |
| 3-Cl | 65–67 |
| 2-CH₃,5-NO₂ | 154 |
| 3,4-Cl₂ | 82–84 |
| 3-Cl,4-NO₂ | 100–104 |
| 4-CH₃ | 74–76 |
| 2-Cl,4-Br | 94–96 |
| 2-Br,4-phenyl | 125 |
| 2,4-(CH₃)₂ | 74 |
| 4-COOCH₃ | 85–88 |
| 2-Cl,4-phenyl | 107 |
| 2,6-Cl₂,4-phenyl | 149–150 |
| 4-phenyl-Cl (4-(4-chlorophenyl)) | 116–118 |
| 2,6-Cl₂,4-(4-bromophenyl) | 150–152 |
| 2-Cl, 6-Br, 4-(4-bromophenyl) | 148–150 |
| 2-Cl,4-(4-chlorophenyl) | 101–102 |
| 2,4,6-Cl₃ | 91–93 |

The reduction according to the invention is carried out with the aid of secondary alcoholates, preferably the secondary alcoholates of aluminum, such as, in particular, aluminum isopropylate, aluminum sec.-butylate and aluminum cyclohexylate.

Preferred diluents for the reaction according to the invention are inert organic solvents, especially alcohols, such as, in particular, isopropanol and sec.-butanol.

The reaction temperatures in the process according to the invention can be varied within a substantial range. In general, the reaction is carried out at about 80° to 120° C., preferably at the boiling point of the solvent.

In carrying out the reaction according to the invention, preferably 0.35 to 1.5 moles of secondary alcoholate are employed per mole of the ketone of the formula (II). To isolate the compounds of the formula (I), the excess solvent is removed by distillation in vacuo and the resulting aluminum compound is decomposed with dilute sulphuric acid. The further working up takes place in the usual manner.

An advantageous procedure is to reduce the triazolylketone of the formula (II) when it is already in the presence of the corresponding form A, whereby the stereoselectivity of the reduction is further shifted in favor of the desired form A. In this method, preferably about 0.5 mole of the corresponding diastereomeric form A and about 0.5 mole of secondary alcoholate are employed per mole of the ketone of the formula (II).

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens. They display a particularly good activity against parasitic fungi on above-ground parts of plants.

As plant protection agents, the active compounds according to the invention can be used particularly successfully for combating smut fungi, for example against the pathogens of bunt of wheat and loose smut of oats, for combating powdery mildew fungi, for example for combating powdery mildew of barley, and for combating species of Venturia, such as the pathogen of apple scab (*Fusicladium dendriticum*).

The partly systemic action of the compounds should be singled out particularly. Thus, it proves possible to protect plants against fungal attack by supplying the active compound to the above-ground parts of the plant via the soil and the root.

As plant protection agents, the compounds according to the invention can be used for the treatment of soil, for the treatment of seed and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.00001 to 0.1 percent by weight, preferably from 0.0001 to 0.05 percent.

For the treatment of seed, amounts of active compound of 0.001 to 50 g, preferably 0.01 to 10 g, are generally employed per kilogram of seed.

For the treatment of soil, amounts of active compound of 1 to 1000 g, preferably 10 to 200 g, are generally employed per cubic meter of soil.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is illustrated in the following examples:

EXAMPLE 1

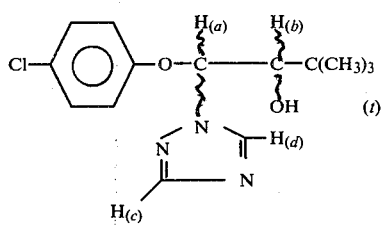

(1) (t)

Form A (enantiomer mixture)

1.47 kg (5 moles) of 1-(4-chlorophenoxy)-3,3-dimethyl-1-(1,2,4-triazol-1-yl)-butan-2-one (technical-grade material, 92.8% strength) were added in portions of 6.25 liters of isopropanol and 611 g (3 moles) of aluminum isopropylate at 50° C. in a 10 liter flange-topped flask equipped with a stirrer, thermometer and a 1 m Vigreux column. After completion of the addition, the mixture was heated to 98° C. bath temperature and 1,000 ml of solvent, and the acetone formed, were distilled off in the course of 13 hours at a temperature of 72° to 79° C. at the column head. The solvent was then distilled off further, under a waterpump vacuum, until half had been removed. The reaction mixture was then added, while stirring, to a mixture of 875 ml of water and 875 ml of 10% strength sulphuric acid. This mixture was stirred for 1.5 hours and the crystals formed were filtered off, washed repeatedly with 300 ml portions of water, and dried. 1.125 kg (76% of theory) of 1-(4-chlorophenoxy)-3,3-dimethyl-1-(1,2,4-triazol-1-yl)-butan-2-ol of melting point 128°–130° C., in which the proportions of diasteromer were 85% of form A and 11.5% of form B, were obtained. A single recrystallization from 2.5 liters of isopropanol gave 600 g (63% of theory, based on the diastereomer mixture) of the pure form A of 1-(4-chlorophenoxy)-3,3-dimethyl-1-(1,2,4-triazol-1-yl)-butan-2-ol, having a melting point of 139° C. and giving the following NMR data:

| δ[ppm]$_{CD_3OD}$ | $H_{(a)}$: 6.46 | (J = 2 Hz) |
|---|---|---|
| | $H_{(b)}$: 3.61 | (J = 2 Hz) |
| | $H_{(t)}$: 1.05 | |
| | $H_{(c)}$: 8.05 | |
| | $H_{(d)}$: 8.52 | |

Analogously, the reaction of 147.8 g (0.5 mol) of 1-(4-chlorophenoxy)-3,3-dimethyl-1-(1,2,4-triazol-1-yl)-butan-2-one in 0.5 liter of butan-2-ol with 49.2 g (0.2 mol) of aluminum sec.-butylate gave, after 10 hours' reaction time at the boil, 75.8% of theory of the pure form A of 1-(4-chlorophenoxy)-3,3-dimethyl-1-(1,2,4-triazol-1-yl)-butan-2-ol, having a melting point of 139° C. and giving the above-mentioned NMR spectrum.

EXAMPLE 2

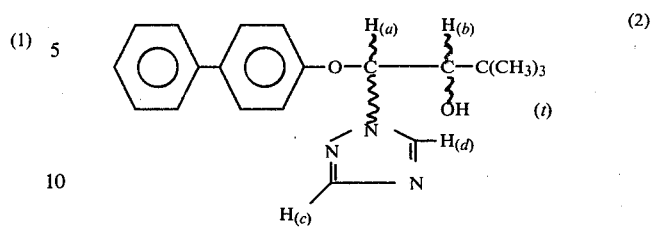

(2) (t)

Form A (enantiomer mixture)

A suspension of 278 g (1.365 moles) of aluminum isopropylate in 2.7 liters of isopropanol was stirred for 1 hour at 60° C. and 760 g (2.27 moles) of 1-(4-biphenylyloxy)-3,3-dimethyl-1-(1,2,4-triazol-1-yl)-butan-2-one were then added incrementally. The mixture was heated for 14 hours to 80° C. while distilling off 260 ml of isopropanol/acetone mixture through a 30 cm Vigreux column. The mixture was then concentrated further by distilling off the solvent in a waterpump vacuum. The residue was taken up in a mixture of 1,000 ml of water, 600 ml of 20% strength sulphuric acid and 3 liter of isopropanol, and the batch was stirred for 1 hour at 20° C., brought to pH 3 with sodium bicarbonate and extracted with 3 liters of methylene chloride. The resultant extract was washed twice with 100 ml of 4% strength sodium hydroxide solution, and with 1.2 liters of water, dried over sodium sulphate and concentrated by distilling off the solvent in a waterpump vacuum. 673 g (88.3% of theory) of 1-(4-biphenylyoxy)-3,3-dimethyl-1-(1,2,4-triazol-1-yl)-butan-2-ol, in which the diastereomer proportions were 73.2% of form A and 19.1% of form B, were obtained. A single recrystallization from 3 liters of isopropanol gave 349.2 g (51.9% of theory, based on the diastereomer mixture) of the pure form A of 1-(4-biphenylyloxy)-3,3-dimethyl-1-(1,2,4-triazol-1-yl)-butan-2-ol, which had a melting point of 136°–137° C. and gave the following NMR data:

| δ[ppm]$_{CD_3OD}$ | $H_{(a)}$: 6.6 | J = 2 Hz) |
|---|---|---|
| | $H_{(b)}$: 3.7 | (J = 2 Hz) |
| | $H_{(t)}$: 1.16 | |
| | $H_{(c)}$: 8.17 | |
| | $H_{(d)}$: 8.6 | |

The forms A of the reduced butan-2-ones of Table 1 can be obtained analogously to Examples 1 and 2.

The fungicidal activity of the compounds of this invention is illustrated by the following examples:

EXAMPLE 3

Seed dressing test/bunt of wheat/field experiment (seedborne mycosis)

To produce a suitable dry dressing, the active compound was extended with a mixture of equal parts by weight of talc and kieselguhr to give a finely powdered mixture with the desired concentration of the active compound.

Dressing was carried out in 4 individual portions, each of 100 g, which were sown on 4 plots of size 5 m². The quoted infection percentages were obtained by completely counting all the diseased panicles on the individual plots and estimating the total number of all panicles by counting the panicles of a few plots with apparently the same crop density.

To test the action against bunt of wheat (*Tilletia caries*), winter wheat (certified seed) was used, which had beforehand been contaminated with 2 g of chlamydospores per kg of seed. Dressing: beginning of October; sowing: Oct. 10–20; evaluation: end of June to middle of July.

The percentages of diseased panicles were in each case based on about 2,000 panicles per plot, equivalent in total to about 8,000 panicles per item of the experiment.

The active compounds, active compound concentrations in the dressing, amount of dressing used and number of diseased panicles can be seen from the table which follows.

individual plots and estimating the total number of all panicles by counting the panicles of a few plots with apparently the same crop density.

To test the action against loose smut of barley (*Ustilago nuda*), naturally contaminated summer barley was used. Dressing and sowing: beginning of April; evaluation: end of June to beginning of July.

The percentages of diseased panicles were in each case based on about 2,000 panicles per plot, equivalent in total to about 8,000 panicles per item of the experiment.

The active compounds, active compound concentrations in the dressing, amount of dressing used and number of diseased panicles can be seen from the table which follows.

TABLE 2

| | Seed dressing test/bunt of wheat/field experiment | | |
|---|---|---|---|
| Active compound | Active compound concentration in the dressing in % by weight | Amount of dressing used in g/kg of seed | Number of panicles with bunt disease in % of the total panicles developed |
| no dressing | — | — | 90.93 |
| 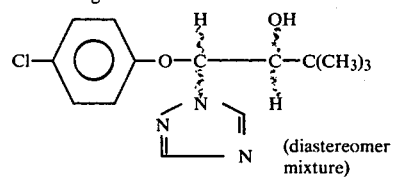 (known) | 15 | 2 | 0.18 |
| Form B (enantiomer mixture) | 15 | 2 | 1.89 |
| Form A (1) (enantiomer mixture) | 15 | 2 | 0.02 | which follows.

TABLE 3

| | Seed dressing test/loose smut of barley/field experiment | | |
|---|---|---|---|
| Active compound | Active compound concentration in the dressing in % by weight | Amount of dressing used in g/kg of seed | Number of panicles with loose smut disease in % of the total panicles developed |
| no dressing | — | — | 29.45 |
| 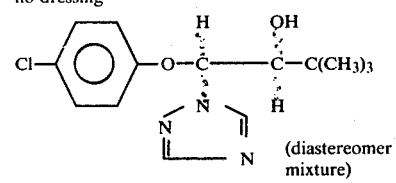 (known) | 10 | 2 | 0.01 |
| Form B (enantiomer mixture) | 10 | 2 | 14.43 |
| Form A (1) (enantiomer mixture) | 10 | 2 | 0.00 |

EXAMPLE 4

Seed dressing test/loose smut of barley/field experiment (seed-borne mycosis)

To produce a suitable dry dressing, the active compound was extended with a mixture of equal parts by weight of talc and kieselguhur to give a finely powdered mixture with the desired concentration of the active compound.

Dressing was carried out in 4 individual portions, each of 100 g, which were sown on 4 plots of size 5 m². The quoted infection percentages were obtained by completely counting all the diseased panicles on the

EXAMPLE 5

Powdery mildew of barley (*Erysiphe graminis* var. Hordei) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. hordei and grown at 21° to 22° C. and 80–90% relative atmospheric humidity and 16 hours' exposure to light. The typical mildew pustules formed on the leaves over the course of 6 days.

The degree of infection was expressed as a percentage of the infection of the untreated control plants. Thus, 0% denoted on infection and 100% denoted the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

verted to percent infection. 0% meant no infection; 100% meant that the plants were totally infected.

The active compounds, the concentrations of the active compounds and the results can be seen from the following table:

TABLE 5

Fusicladium test (apple)/protective

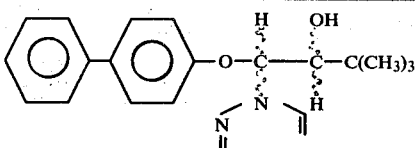

| Active compound | Infection in % at an active compound concentration of 0.0005% |
|---|---|
| (diastereomer mixture) | 32 |

TABLE 4

Powdery mildew of barley test (*Erysiphe graminis* var. *hordei*)/systemic
(known)

| Active compound | Active compound concentration in the dressing in % by weight | Amount of dressing used in g/kg of seed | Infection in % of the untreated control |
|---|---|---|---|
| no dressing | — | — | 100 |
| 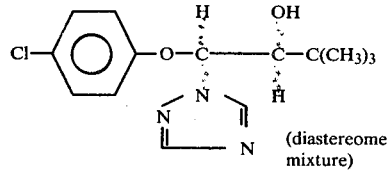 (known) | 0.25 | 2 | 26.3 |
| Form B (enantiomer mixture) | 0.25 | 2 | 81.7 |
| Form A (1) (enantiomer mixture) | 0.25 | 2 | 4.2 |

EXAMPLE 6

Fusicladium test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18°–20° C. and at a relative atmospheric humidity of 100%.

The plants were then brought into a greenhouse again for 14 days.

15 days after inoculation, the infection of the seedlings was determined. The assessment data were con-

| Form B (enantiomer mixture) | 36 |
| Form A (1) (enantiomer mixture) | 5 |

It will be appreciated that the instant specification and examples are set forth by way of illustration and not limitation, and that various modifications and changes may be made without departing from the spirit and scope of the present invention.

What we claim is:

1. The substantially pure diastereomeric form A of a triazolyl-O,N-acetal selected from the group consisting of 1-(4-chlorophenoxy)-3,3-dimethyl-1-(1,2,4-triazol-1-yl)-butan-2ol and 1-(4-biphenylyloxy)-3,3-dimethyl-1-(1,2,4-triazol-1-yl)-butan-2-ol.

2. The substantially pure diastereomeric form A of a compound according to claim 1, wherein such compound is 1-(4-chlorophenoxy)-3,3-dimethyl-1-(1,2,4-triazol-1-yl)-butan-2-ol of the formula

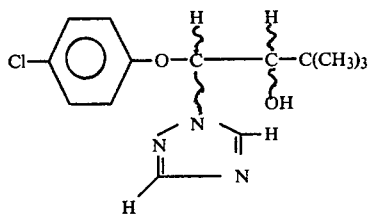

3. The substantially pure diastereomeric form A of a compound according to claim 1, wherein such compound is 1-(4-biphenylyloxy)-3,3-dimethyl-1-(1,2,4-triazol-1-yl)-butan-2-ol, of the formula

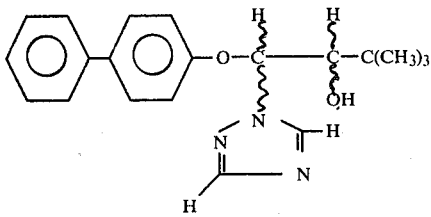

4. A fungicidal composition containing as active ingredient the substantially pure diastereomeric form of a compound according to claim 1 in admixture with a diluent.

5. A method of combating fungi which comprises applying to the fungi, or to a habitat thereof, the substantially pure diastereomeric form of a compound according to claim 1.

6. The method according to claim 5, in which said compound is 1-(4-chlorophenoxy)-3,3-dimethyl-1-(1,2,4-triazol-1-yl)-butan-2-ol.

7. The method according to claim 5, in which said compound is 1-(4-biphenylyloxy)-3,3-dimethyl-1-(1,2,4-triazol-1yl)-butan-2-ol.

* * * * *